(12) United States Patent
Dohda et al.

(10) Patent No.: US 11,976,301 B2
(45) Date of Patent: May 7, 2024

(54) METHOD FOR PRODUCING CULTURE CONTAINING MEGAKARYOCYTES, AND METHOD FOR PRODUCING PLATELETS USING SAME

(71) Applicants: Megakaryon Corporation, Kyoto (JP); Kyoto University, Kyoto (JP)

(72) Inventors: Takeaki Dohda, Kyoto (JP); Sachiko Kobayashi, Kyoto (JP); Koji Eto, Kyoto (JP); Hiroshi Endo, Kyoto (JP); Sou Nakamura, Kyoto (JP)

(73) Assignees: Megakaryon Corporation, Kyoto (JP); Kyoto University, Kyoto (JP)

( * ) Notice: Subject to any disclaimer, the term of this patent is extended or adjusted under 35 U.S.C. 154(b) by 223 days.

(21) Appl. No.: 17/209,035

(22) Filed: Mar. 22, 2021

(65) Prior Publication Data

US 2021/0222124 A1  Jul. 22, 2021

Related U.S. Application Data

(63) Continuation of application No. 15/555,626, filed as application No. PCT/JP2016/057467 on Mar. 9, 2016, now abandoned.

(30) Foreign Application Priority Data

Mar. 9, 2015 (JP) ................................ 2015-046281

(51) Int. Cl.
*C12N 5/00* (2006.01)
*C12N 5/078* (2010.01)

(52) U.S. Cl.
CPC ........ *C12N 5/0644* (2013.01); *C12N 2500/25* (2013.01); *C12N 2500/38* (2013.01); *C12N 2501/125* (2013.01); *C12N 2501/145* (2013.01); *C12N 2501/727* (2013.01); *C12N 2501/998* (2013.01); *C12N 2506/45* (2013.01); *C12N 2510/00* (2013.01)

(58) Field of Classification Search
CPC .................................................. C12N 5/0644
See application file for complete search history.

(56) References Cited

U.S. PATENT DOCUMENTS

| | | |
|---|---|---|
| 2012/0238023 A1 | 9/2012 | Eto et al. |
| 2014/0227780 A1 | 8/2014 | Nishino et al. |
| 2016/0002599 A1 | 1/2016 | Eto |

FOREIGN PATENT DOCUMENTS

| | | |
|---|---|---|
| WO | 1999061588 A1 | 12/1999 |
| WO | 2011034073 A1 | 3/2011 |
| WO | 2011071085 A1 | 6/2011 |
| WO | 2013051625 A1 | 4/2013 |
| WO | 2013190296 A | 12/2013 |
| WO | 2014123242 A1 | 8/2014 |

OTHER PUBLICATIONS

Ravid et al. (1993) "Selection of an HEL-Derived Cell Line Expressing High Levels of Platelet Factor 4", Blood, vol. 81, No. 11, pp. 2885-2890. (Year: 1993).*
Panuganti et al. (2013) "Three-stage ex vivo expansion of high-ploidy megakaryocytic cells: toward large-scale platelet production" Tissue engineering Part A, 19(7-8), 998-1014. (Year: 2013).*
Nakamura et al. (Feb. 2014) "Expandable Megakaryocyte Cell Lines Enable Clinically Applicable Generation of Platelets from Human Induced Pluripotent Stem Cells" Cell stem cell, 14(4), 535-548. (Year: 2014).*
Martin et al. (1982) "HEL Cells: A New Human Erythroleukemia Cell Line with Spontaneous and Induced Globin Expression", Science, vol. 216, No. 4551, pp. 1233-1235. (Year: 1982).*
Debili et al. (2001) "Different expression of CD41 on human lymphoid and myeloid progenitors from adults and neonates" Blood, The Journal of the American Society of Hematology, 97(7), 2023-2030. (Year: 2001).*
Fang et al. (2005) "Therapeutic expression of the platelet-specific integrin, αIIbβ3, in a murine model for Glanzmann thrombasthenia", Blood, 106(8), 2671-2679. (Year: 2005).*
Murphy et al. (1999) "A model for studying megakaryocyte development and biology", Proc. Natl. Acad. Sci. USA, vol. 96, No. 6, pp. 3065-3070. (Year: 1999).*
Cheng et al. (2012) "Protecting against wayward human induced pluripotent stem cells with a suicide gene", Biomaterials 33(11), 3195-3204. (Year: 2012).*
Abujarour et al. (2013) "Optimized surface markers for the prospective isolation of high-quality hiPSCs using flow cytometry selection" Scientific reports, 3(1), 1179, 11 pages. (Year: 2013).*
Daniels, G. (2007) "Functions of red cell surface proteins" Vox sanguinis, 93(4), 331-340. (Year: 2007).*
Rahuel et al. (1994) "Post-transcriptional regulation of the cell surface expression of glycophorins A, B, and E" Journal of Biological Chemistry, 269(52), 32752-32758. (Year: 1994).*
Feng et al. (2014) "Scalable generation of universal platelets from human induced pluripotent stem cells" Stem cell reports, 3(5), 817-831. (Year: 2014).*
Takayama et al., "Generation of functional platelets from human embryonic stem cells in vitro via ES-sacs, VEGF- promoted structures that concentrate hematopoietic proge", Jun. 1, 2008, pp. 5298-5306, vol. 111, No. 11, Publisher: Blood.
Cheng, et al., "Protecting against wayward human induced pluripotent stem cells with a suicide gene", Jan. 24, 2012, pp. 3195-3204, vol. 33, No. 11, Publisher: Biomaterials.

(Continued)

*Primary Examiner* — James D Schultz
*Assistant Examiner* — James Joseph Graber
(74) *Attorney, Agent, or Firm* — Suzannah K. Sundby, Esq.; Canady + Lortz LLP

(57) ABSTRACT

The present invention provides a method for producing megakaryocytes that have an increased capacity to produce platelets, the method comprising a step of culturing, under conditions that cause the death of cells that do not express a gene that is specifically expressed by megakaryocytes, cells that have the capacity to differentiate into megakaryocytes.

7 Claims, 11 Drawing Sheets

Specification includes a Sequence Listing.

(56) References Cited

OTHER PUBLICATIONS

International Search Report received in PCT/JP2016/057467, dated Jun. 7, 2016.
Written Opinion received in PCT/JP2016/057467, dated Jun. 7, 2016.
Fang et al., "Therapeutic expression of the platelet-specific integrin, alphaIIbbeta3, in a murine model for Glanzmann thrombasthenia", 2005, pp. 2671-2679, vol. 106, No. 8, Publisher: Blood.
Karagiannis and Eto, "Manipulating megakaryocytes to manufacture platelets ex vivo", Jun. 19, 2015, pp. 847-S53, vol. 13, No. Suppl 1, Publisher: J Thromb Haemost.
Martin & Papayannopoulou, "Hel cells: a new human erythroleukemia cell line with spontaneous and induced globin expression", Jun. 11, 1982, pp. 1233-1235, vol. 216, No. 4551, Publisher: Science.
Murphy & Leavitt, "A model for studying megakaryocyte development and biology", 1999, pp. 3065-3070, vol. 96, No. 6, Publisher: Proc Natl Acad Sci U S A.
Nakamura, et al., "Expandable megakaryocyte cell lines enable clinically applicable generation of platelets from human induced pluripotent stem cells", Apr. 3, 2014, pp. 535-548, vol. 14, No. 4, Publisher: Cell Stem Cell.
Ravid et al., "Selection of an HEL-derived cell line expressing high levels of platelet factor 4", Jun. 1, 1993, pp. 2885-2890, vol. 81, No. 11, Publisher: Blood.
Machlus & Italiano Je, The incredible journey: From megakaryocyte development to platelet formation, Jun. 10, 2013, pp. 785-796, vol. 201, No. 6, Publisher: J Cell Biol.

\* cited by examiner

11,976,301 B2

METHOD FOR PRODUCING CULTURE CONTAINING MEGAKARYOCYTES, AND METHOD FOR PRODUCING PLATELETS USING SAME

CROSS-REFERENCE TO RELATED APPLICATIONS

This application is a continuation of U.S. patent application Ser. No. 15/555,626, filed Sep. 5, 2017, which is herein incorporated by reference in its entirety. U.S. Ser. No. 15/555,626 is a 371 national phase entry of PCT/JP2016/057467, which claims priority to JP 2015-046281, filed Mar. 9, 2015.

REFERENCE TO A SEQUENCE LISTING SUBMITTED VIA EFS-WEB

The content of the ASCII text file of the sequence listing named "20170905_101621_001US1_seq", which was filed in PCT/JP2016/057467 on Mar. 9, 2016 and downloaded from the WIPO database, is 1.58 kb in size with a created date of Sep. 5, 2017, and electronically submitted via EFS-Web herewith the application, is incorporated herein by reference in its entirety.

TECHNICAL FIELD

The present invention relates to a method for producing a culture that contains megakaryocytes and to a method for producing platelets using the same.

BACKGROUND ART

The treatment of blood-related diseases or surgical treatments require that blood cells be supplied to the treatment. The following cells are in particularly high demand among blood cells: platelets, which are cells essential for blood coagulation (hemostasis); proplatelets; and megakaryocyte cells, which are cells that produce platelets. There is great demand for platelets in particular in, e.g., leukemia, bone marrow transplantation, and anticancer therapies, and there is thus strong demand for a stable supply.

Pluripotent stem cells, e.g., ES cells and iPS cells, are used as a source for the artificial production of blood cells such as platelets. In recent years, due to the establishment of iPS cells, the usefulness of pluripotent stem cells as an important source in cell therapies in regenerative medicine has been receiving greater attention. To date, for example, Takayama et al. have been successful in inducing the differentiation of megakaryocyte cells and platelets from human ES cells (Takayama N. et al., Blood, 111, pp. 5298-5306, 2008).

CITATION LIST

Non-Patent Documents

Non-Patent Document 1: Takayama N. et al., Blood, 111, pp. 5298-5306, 2008

SUMMARY

Technical Problem

Cytokines such as thrombopoietin (TPO) can specifically induce the differentiation of hematopoietic progenitor cells to megakaryocyte cells (Takayama N. et al., Blood (ibid)). However, the long-term maintenance of the differentiation phenotype (CD41a-positive, CD42a-positive, or CD42b-positive) by the megakaryocyte cells produced by conventional differentiation induction methods has been problematic.

Solution to Problem

The present inventors carried out the induction of differentiation to megakaryocyte cells under conditions that caused the death only of cells that did not express a megakaryocyte-specific cell surface marker, and unexpectedly discovered that the resulting megakaryocyte cells could stably maintain their differentiation phenotype on an extended basis and that these cells exhibited a very high per-cell capacity to produce platelets. The present invention was achieved based on this discovery.

Thus, the present application encompasses the following inventions.

[1] A method for producing a culture of megakaryocytes or megakaryocyte progenitor cells, the method containing:
a step of culturing, under conditions that cause the death of cells that do not express a gene that is specifically expressed by megakaryocytes, a cell group that contains megakaryocytes or cells having the capacity to differentiate into megakaryocytes.

[2] The method according to [1], wherein the cell group has been transformed by a gene for resistance to a drug that exhibits cytotoxicity, the drug resistance gene being positioned under the control of a promoter of the gene that is specifically expressed by megakaryocytes, and the drug being added in the culture step.

[3] The method according to [1], wherein the cell group has been transformed by a gene that causes the death of the cells that do not express the gene that is specifically expressed by megakaryocytes, and this gene is positioned under the control of a promoter of a gene that is specifically expressed by the cells that do not express the gene that is specifically expressed by megakaryocytes.

[4] The method according to any of [1] to [3], wherein the gene that is specifically expressed by megakaryocytes is a gene that codes for a cell surface marker that is specifically expressed by megakaryocytes.

[5] The method according to [4], wherein the cell surface marker that is specifically expressed by megakaryocytes is CD41a, CD42a, and/or CD42b.

[6] The method according to any of [1] to [5], wherein the cells having the capacity to differentiate into megakaryocytes are at least one type selected from the group consisting of hematopoietic stem cells, hematopoietic progenitor cells, CD34-positive cells, and megakaryocyte progenitor cells.

[7] The method according to any of [1] to [6], wherein the culture step is carried out in the absence of serum and/or feeder cells.

[8] The method according to any of [1] to [7], wherein the megakaryocytes in the culture to be produced retain the differentiation phenotype thereof, and have an increased platelet production capacity.

[9] The method according to any of [2] to [8], wherein the cell group is transformed by a vector in which the promoter and the drug resistance gene or a lethal gene are operably linked.

[10] The method according to any of [2] and [4] to [9], wherein the drug resistance gene is at least one type selected from the group consisting of a puromycin resistance gene, a neomycin resistance gene, a kanamycin resistance gene, a chloramphenicol resistance gene, an erythromycin resistance gene, a tetracycline resistance gene, a hygromycin resistance gene, an ampicillin resistance gene, a Zeocin™ resistance gene, a blasticidin S resistance gene, and a histidinol resistance gene.

[11] The method according to any of [3] to [9], wherein the lethal gene is at least one type selected from the group consisting of the HSV-TK gene, cytochrome C gene, and Mule/ARF-BP-1 gene.

[12] The method according to any of [1] to [11], wherein the culture step is carried out in a culture medium containing TPO and SCF.

[13] The method according to [1], wherein the cell group contains cells produced by the introduction of c-MYC, BMI1, and BCL-xL to hematopoietic progenitor cells.

[14] A method for producing platelets, the method using megakaryocytes produced by the method described in any of [1] to [10].

[15] A culture expansion method for megakaryocytes or megakaryocyte progenitor cells, the method containing:
a step of culturing, under conditions that cause the death of cells that do not express a gene that is specifically expressed by megakaryocytes, a cell group that contains megakaryocytes or cells having the capacity to differentiate into megakaryocytes.

[16] The method according to [15], wherein the cell group has been transformed by a gene for resistance to a drug that exhibits cytotoxicity, the drug resistance gene being positioned under the control of a promoter of the gene that is specifically expressed by megakaryocytes, and the drug being added in the culture step.

[17] The method according to [15] or [16], wherein the gene that is specifically expressed by megakaryocytes is a gene that codes for a cell surface marker that is specifically expressed by megakaryocytes.

[18] The method according to [17], wherein the cell surface marker that is specifically expressed by megakaryocytes is CD41a, CD42a, and/or CD42b.

[19] The method according to any of [15] to [18], wherein the cells having the capacity to differentiate into megakaryocytes are at least one type selected from the group consisting of hematopoietic stem cells, hematopoietic progenitor cells, CD34-positive cells, and megakaryocyte progenitor cells.

[20] The method according to any of [15] to [19], wherein the culture step is carried out in the absence of serum and/or feeder cells.

[21] The method according to any of [15] to [20], wherein after the expansion culture, the megakaryocytes retain the differentiation phenotype thereof, and have an increased platelet production capacity.

[22] The method according to any of [15] to [21], wherein the cell group is transformed by a vector in which the promoter and the drug resistance gene or a lethal gene are operably linked.

[23] The method according to any of [15] to [22], wherein the drug resistance gene is at least one type selected from the group consisting of a puromycin resistance gene, a neomycin resistance gene, a kanamycin resistance gene, a chloramphenicol resistance gene, an erythromycin resistance gene, a tetracycline resistance gene, a hygromycin resistance gene, an ampicillin resistance gene, a Zeocin™ resistance gene, a blasticidin S resistance gene, and a histidinol resistance gene.

[24] The method according to any of [15] to [23], wherein the culture step is carried out in a culture medium containing TPO and SCF.

[25] The method according to any of [15] to [24], wherein the cell group contains cells produced by the introduction of c-MYC, BMI1, and BCL-xL to hematopoietic progenitor cells.

[26] A culture produced by the cultivation, under conditions that cause the death of cells that do not express a gene that is specifically expressed by megakaryocytes, of a cell group that contains megakaryocytes or cells having the capacity to differentiate into megakaryocytes.

Advantageous Effects of Invention

The production method according to the present invention produces megakaryocyte cells that have the ability to retain the differentiation phenotype on a long-term basis. Not only is the amount of platelet production per cell population increased through the elimination of cells that would differentiate into other cell lines during the production process, but the megakaryocytes provided by the present invention are very surprising in terms of having an increased platelet productivity per cell. From these perspectives, the production method according to the invention of the present application can be said to be very useful over the prior art.

In addition, the production method according to the present invention can also bring about an improvement in the efficiency of establishment of megakaryocyte cell lines that have a self-replication capacity. Moreover, the production method according to the present invention can also bring about the proliferation of a megakaryocyte cell line in large amounts without any use of serum or feeder cells and thus, is also advantageous in that it suppresses the appearance of the problem of immunogenicity when the obtained platelets are used clinically. Suspension culture, e.g., in flasks and so forth, is possible when the cell culture or platelet production can be run without using feeder cells, and as a result the production costs can be restrained and the mass production of platelets is also made possible.

Figure 1:
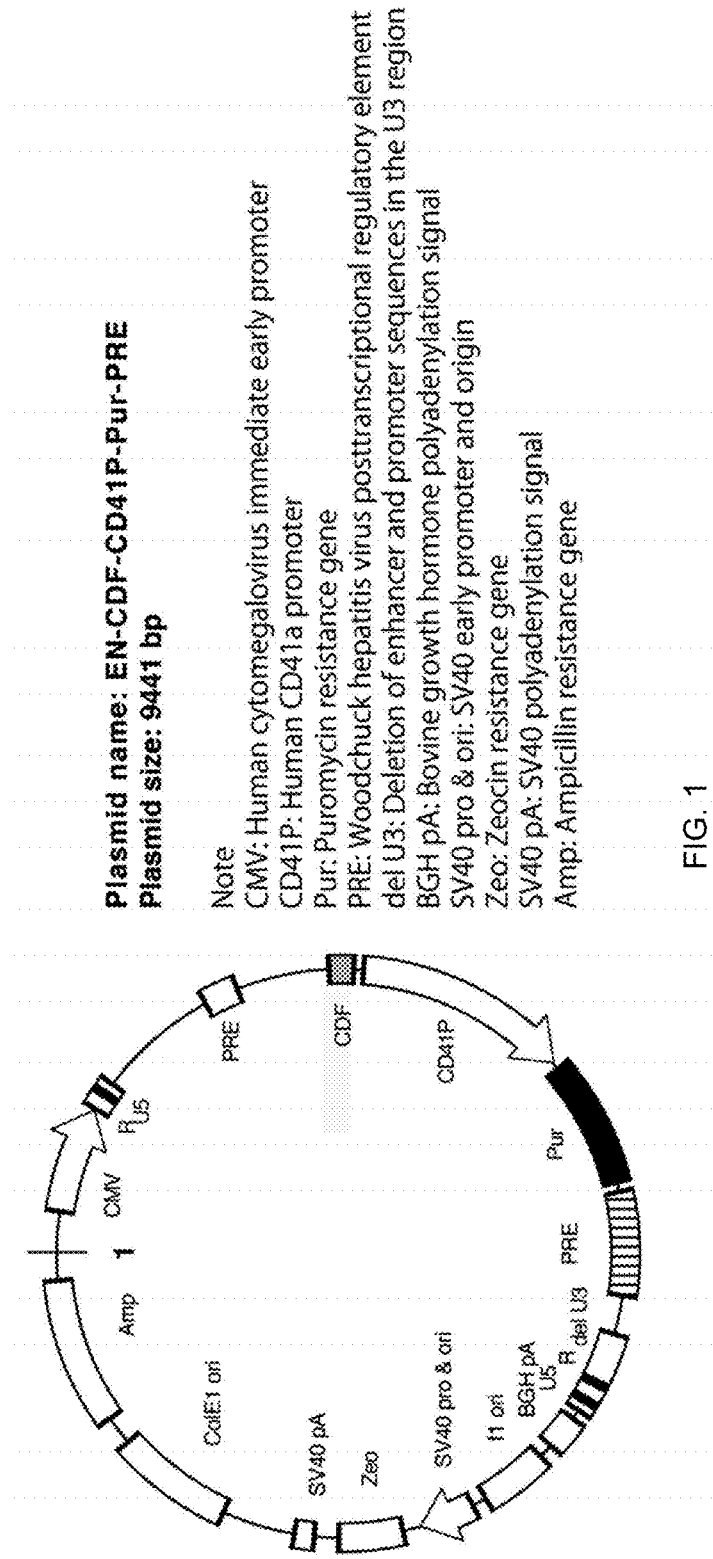
FIG. 1 illustrates a CD41a promoter-puromycin lentivirus vector.

DESCRIPTION OF EMBODIMENTS (Method for Producing Megakaryocyte Cells)

The megakaryocyte production method according to the present invention contains a step of culturing, under conditions that cause the death of cells that do not express a gene that is specifically expressed by megakaryocytes, a cell group that contains megakaryocytes or cells having the capacity to differentiate into megakaryocytes. The gene that is specifically expressed by megakaryocytes can be exemplified by cell surface markers, e.g., CD41a, CD42a, CD42b, CD9, CD61, and CD62P, and by GATA1, NF-E2, β-tubulin, platelet factor 4, and so forth, which are genes that are specifically expressed by megakaryocyte cells. The conditions lethal for cells that do not express a gene specifically expressed by megakaryocyte cells should be conditions that exercise lethality only on cells other than megakaryocytes or cells that do not differentiate into megakaryocytes, while not exercising lethality on cells that differentiate into megakaryocytes, megakaryocyte progenitor cells, megakaryocyte cells, mature megakaryocyte cells, and so forth, but these conditions are not otherwise particularly limited. The following, for example, may be envisioned: a system in which drug resistance is imparted only to megakaryocyte cells, megakaryocyte progenitor cells, and so forth, followed by killing unwanted cells with the corresponding drug; or a system in which a lethal gene is expressed only in unwanted cells.

Thus, in a first embodiment of the present invention, using a culture system in which a drug resistance gene is driven by a promoter that is specifically activated in megakaryocyte cells, only cells that do not express the gene that is specifically expressed by megakaryocytes can be killed by the cultivation, in the presence of the corresponding drug, of a cell group containing megakaryocyte cells or cells having the capacity to differentiate into megakaryocyte cells. Such a culture system can be constructed, for example, by placing a drug resistance gene under the control of a promoter for a gene that is specifically expressed by megakaryocyte cells. As a result, drug resistance can be imparted only to cells that express megakaryocyte-specific cell surface markers. In a preferred embodiment, drug resistance is conferred through the introduction into the cells before cultivation of a vector in which the promoter is operably linked with a drug resistance gene positioned downstream therefrom.

The promoter region of the integrin αIIBβ3 (CD41a) gene is an example of a promoter that is specifically activated in megakaryocyte cells (Wilcox D. A., et al., Blood (2000), Fang J., et al., Blood (2005)). Besides this, the following may also be used in the present invention: promoters for the CD42a gene, CD42b gene, and so forth, which are cell surface markers that are specifically expressed by megakaryocyte cells, or promoters for the genes encoding GATA1, NF-E2, β-tubulin, platelet factor 4, and so forth, which are genes that are specifically expressed by megakaryocyte cells.

The drug resistance gene can be exemplified by the puromycin resistance gene, neomycin resistance gene, kanamycin resistance gene, chloramphenicol resistance gene, erythromycin resistance gene, tetracycline resistance gene, hygromycin resistance gene, ampicillin resistance gene, Zeocin™ resistance gene, blasticidin S resistance gene, and histidinol resistance gene. The drug corresponding to each of the genes is added to the culture medium after the cells have been transformed with the gene prior to cultivation.

In a second embodiment of the present invention, using a culture system wherein a lethal gene is driven by a promoter specific to cells that do not express a gene that is specifically expressed by megakaryocytes, the megakaryocyte cells can be effectively concentrated by causing the death of only cells in which this promoter functions by culturing the megakaryocyte cells or cells capable of differentiating into megakaryocyte cells. Such a promoter can be exemplified by promoters for cell surface markers (for example, CD235 in the case of erythrocytes) specific to cells that do not express megakaryocyte-specific cell surface markers. Cells that do not differentiate into megakaryocyte cells can be removed by positioning a lethal gene, e.g., the HSV-TK gene, cytochrome C gene, and Mule/ARF-BP-1 gene, under the control of such a promoter and thereby driving the lethal gene.

The expression of the drug resistance gene or lethal gene can be regulated using an inducible gene expression system, for example, the Tet-on (registered trademark) system or Tet-off (registered trademark) system.

In this embodiment, the cell group containing megakaryocytes or cells having the capacity to differentiate into megakaryocytes is transformed with the target gene. When the target gene is overexpressed in the cell during the culture step of the present invention, this step can be carried out by a person skilled in the art using known methods. Expression may be brought about by transducing the target gene into the cells using, for example, a lentivirus- or retrovirus-based gene transduction virus. When gene expression is carried out using a virus-based gene transduction system, the vector can contain the target gene operably linked on the downstream side of a suitable promoter. Here, "operably" linked means that the target gene is cis-directed by the promoter and the promoter and target gene are linked such that a desired expression of the target gene is realized. In embodiments of the present invention, for example, the target gene may be constitutively expressed using, e.g., the CMV promoter, EF1 promoter, and so forth; or, a suitable promoter (an inducible promoter) can be positioned under the direction of an element that is actively controlled by a trans factor, e.g., a drug response element, e.g., for tetracycline, and, for example, the target gene can also be inducibly expressed through control of, e.g., drug addition. A person skilled in the art seeking to realize control of the expression of a desired target gene can easily select a suitable system from among the numerous currently available gene expression systems. A commercially available kit and so forth may be used. In addition, the oncogene described below and so forth and the drug resistance gene or lethal gene that is the target gene for expression control may be inserted on different vectors from each other or may be inserted on the same vector.

The inhibition of gene expression within the megakaryocyte cells may be achieved by, for example, deactivating the induction of expression by the aforementioned inducible expression system, by removing, for example, the drug. Or, an inhibitory control may be exercised on gene expression by removal of, for example, the introduced oncogene, using, for example, the Cre/lox system. For example, a commercial kit may also be used as appropriate to exercise inhibitory regulation of gene expression.

As used herein, "cells having the capacity to differentiate into megakaryocytes" refers to cells that originate from hematopoietic stem cells and can undergo differentiation into megakaryocytes depending on the differentiation induction conditions. Examples here are hematopoietic stem cells, hematopoietic progenitor cells, CD34-positive cells, megakaryocyte-erythroid progenitor cells (MEP), megakaryocyte progenitor cells, and so forth. Cells having the capacity to differentiate into megakaryocytes can be obtained by known methods; for example, they can be obtained by isolation from bone marrow, umbilical cord blood, peripheral blood, and so forth, and can also be obtained by inducing differentiation from pluripotent stem cells, e.g., ES cells and iPS cells. When hematopoietic progenitor cells are used as the cells having the capacity to differentiate into megakaryocytes, c-MYC, BMI1, and BCL-xL may be introduced into the cells in advance prior to the culture step according to the present invention.

Cells that do not express cell surface markers specific to megakaryocyte cells include CD41-negative/CD42-negative cells, which ultimately do not differentiate into megakaryocytes, for example, erythrocytes or their progenitor cells, but are not necessarily limited to cells derived from hematopoietic stem cells. For example, in an embodiment that uses a drug resistance gene, drug resistance is conferred only on cells having the capacity to differentiate into megakaryocytes, and thus all the other cells can be eliminated.

The megakaryocytes in the culture produced by the present invention can be present as a cell population that includes not only megakaryocyte cells, but also megakaryocyte progenitor cells that prior to maturation have an inadequate platelet production capacity, megakaryocyte cells which multinucleation has progressed, and so forth. Among the total cells present in the culture, the proportion taken up by megakaryocytes or megakaryocyte progenitor cells and particularly by megakaryocytes is preferably at least 50%, for example, at least 60%, at least 70%, at least 80%, or at least 90%. The obtained megakaryocytes provide a significantly higher platelet productivity per cell than megakaryocytes obtained by conventional methods in which cells not expressing cell surface markers specific to megakaryocyte cells are not removed. While the level of the increase in the platelet productivity varies with the culture conditions, the productivity is several times that of conventional methods; for example, the productivity can be increased at least 5-fold. The increase in platelet productivity is calculated by comparison of the amount of platelet production, per seeded cell, by CD41a-positive cells and preferably CD41a-positive and CD42b-positive cells. The presence/absence of functionality by the obtained platelets can be confirmed by known methods, for example, the amount of activated platelets can be measured using PAC-1, which is an antibody that binds to only the human integrin αIIBβ3 on the activated platelet membrane.

The megakaryocytes obtained according to the present invention can stably maintain their differentiation phenotype on a longer term basis than megakaryocytes induced by conventional methods. The retention of the differentiation phenotype can be evaluated, for example, using the proportion of cells that express megakaryocyte markers. After the passage of some particular period of time, megakaryocytes obtained in accordance with the present invention have a higher proportion of megakaryocyte marker (CD41a, CD42a, CD42b, and so forth)-positive cells than megakaryocytes induced by conventional methods. In addition, for example, megakaryocytes produced in accordance with the present invention can also more stably maintain their differentiation phenotype for at least 90 days than megakaryocytes induced by conventional methods. The present invention can also bring about an improved efficiency of establishment of megakaryocyte cell lines that exhibit a self-replication capacity.

The culture step used in the present invention may be carried out in the presence or in the absence of feeder cells. The feeder cells should be cells that enable the induction of megakaryocytes or megakaryocyte progenitor cells, but are not otherwise particularly limited, and can be exemplified by C3H10T1/2 (Katagiri T., et al., Biochem. Biophys. Res. Commun. 172, 295-299 (1990)). As a general matter, the platelet productivity of megakaryocyte progenitor cells is improved when feeder cells are used, but the megakaryocytes produced by the present invention offer the advantage of being able to produce platelets at about the same level per cell regardless of whether feeder cells are used or not.

The culture medium used in the present invention, although not particularly limited, can be prepared based on culture media used for the cultivation of animal cells as basal media. The basal media include, for example, IMDM medium, Medium 199, Eagle's Minimum Essential Medium (EMEM), αMEM medium, Dulbecco's Modified Eagle's Medium (DMEM), Ham's F12 medium, RPMI 1640 medium, Fischer's medium, Neurobasal Medium (Life Technologies Corporation), and mixed culture media from the preceding. The culture medium may contain serum or may be serum-free. As necessary, the culture medium may also contain at least one substance from, for example, albumin, insulin, transferrin, selenium, fatty acids, trace elements, 2-mercaptoethanol, thioglycerol, lipids, amino acids, L-glutamine, nonessential amino acids, vitamins, growth factors, low molecular weight compounds, antibiotics, antioxidants, pyruvic acid, buffers, inorganic salts, and cytokines. The cytokines are proteins that promote blood cell differentiation and can be exemplified by VEGF, TPO, SCF, and so forth. IMDM medium containing serum, insulin, transferrin, selenium, thioglycerol, ascorbic acid, and TPO is a preferred medium for the present invention. More preferably, SCF is additionally contained. When an expression vector containing a drug-responsive promoter, such as the Tet-on (registered trademark) system or Tet-off (registered trademark) system, is used, the corresponding drug, for example, tetracycline or doxycycline, is preferably incorporated in the medium in the overexpression step.

The culture conditions, although not particularly limited, may be, for example, those in which the cells are cultured in the presence of TPO (10 to 200 ng/mL and preferably about 50 to 100 ng/mL), or in the presence of TPO (10 to 200 ng/mL and preferably about 50 to 100 ng/mL) and SCF (10 to 200 ng/mL and preferably about 50 ng/mL), or in the presence of TPO (10 to 200 ng/mL and preferably about 50 to 100 ng/mL) and SCF (10 to 200 ng/mL and preferably about 50 ng/m L) and heparin (10 to 100 U/mL and preferably about 25 U/mL). With regard to the culture temperature, it is recognized that the differentiation of megakaryocytes or megakaryocyte progenitor cells is promoted by culture at a temperature of at least 35.0° C. The culture temperature is a temperature that does not damage the cells, and, for example, 35.0° C. to 42.0° C. is preferred, 36.0° C. to 40.0° C. is more preferred, and 37.0° C. to 39.0° C. is still more preferred.

An appropriate culture time can be determined by a person skilled in the art while monitoring, for example, the number of megakaryocytes or megakaryocyte progenitor cells. For example, the proportion of megakaryocyte cells in the culture can be determined by using flow cytometry to analyze cell surface markers that are specifically expressed by megakaryocytes, and, for example, culture may be carried out to bring the proportion taken up by megakaryocytes or megakaryocyte progenitor cells and particularly by megakaryocytes to at least 50%, for example, at least 60%, at least 70%, at least 80%, or at least 90% of the total cells present in the culture. The number of days, although not particularly limited as long as the desired megakaryocyte progenitor cells are obtained, is, for example, preferably at least 3 days, more preferably at least 6 days, and even more preferably at least 9 days. However, because long culture times do not cause problems, this may be at least 12 days, at least 18 days, at least 24 days, at least 30 days, at least 42 days, at least 48 days, at least 54 days, or at least 60 days. Subculturing is desirably carried out as appropriate during the culture period.

The following drugs, for example, can be used when the cells are transformed by a drug resistance gene: puromycin, neomycin, kanamycin, chloramphenicol, erythromycin, tetracycline, hygromycin, ampicillin, Zeocin™, blasticidin S, or histidinol.

Insofar as the effects of the present invention are not impaired, the art with regard to megakaryocyte production known to a person skilled in the art can be applied to the production method of the present invention. For example, in an embodiment of the method of the present invention for producing megakaryocytes, the medium may additionally contain (a) a substance that inhibits the expression or function of the p53 gene product, (b) an inhibitor of actomyosin complex functionality, (c) a ROCK inhibitor, and (d) an HDAC inhibitor. These methods can be carried out in accordance with the method described in, for example, WO 2012/157586.

Moreover, as described in WO 2011/034073, the amount of megakaryocyte cell production can also be increased by overexpressing oncogenes, e.g., the c-MYC gene, and/or exogenous genes, e.g., the polycomb gene. In such an embodiment, the production method of the invention according to this application may additionally contain a step of turning off the overexpression in the megakaryocytes or megakaryocyte progenitor cells and culturing. With regard to the method for turning off the overexpression, for example, when overexpression is performed using a drug-responsive vector, the turn-off of overexpression may be achieved by eliminating contact between the corresponding drug and the cells. Otherwise, when a vector containing LoxP, see above, is used, the turn-off of overexpression may be achieved by the introduction of Cre recombinase into the cells. When the introduction of a transient expression vector and introduction of RNA or protein are used, the turn-off of overexpression may be achieved by stopping contact with the vector, etc. The culture medium used in this step may be the same as the culture media described above.

The conditions during culture with the turn-off of overexpression are not particularly limited, but, for example, 35.0° C. to 42.0° C. is preferred, 36.0° C. to 40.0° C. is more preferred, and 37.0° C. to 39.0° C. is even more preferred.

The culture time after the turn-off of overexpression can be determined as appropriate while monitoring, for example, the cell count and particularly the megakaryocyte cell count; however, it is preferably at least 2 days after the turn-off of overexpression, for example, 2 to 14 days. This culture time is more preferably 3 to 12 days and is still more preferably 4 to 10 days. Culture medium exchange or subculture is desirably carried out as appropriate during the culture period.

The megakaryocytes obtained in accordance with the present invention, upon undergoing sufficient maturation, can produce functional platelets at good efficiencies. As used herein, maturation of the megakaryocyte refers to the megakaryocyte undergoing a sufficient multinucleation to be able to produce functional platelets. Megakaryocyte maturation can also be confirmed by, for example, an increase in the expression of a megakaryocyte maturation-related gene group such as GATA1, p45 NF-E2 and beta1-tubulin, the formation of proplatelets, and multinucleation within the cells. These platelets have already been confirmed in vivo and in vitro to have a high thrombogenicity.

Moreover, the megakaryocyte and/or megakaryocyte progenitor cells can produce functional platelets even after cryopreservation and thawing. The megakaryocyte cell lines produced with the present invention can be distributed in a cryopreserved state.

(Method for Producing Platelets)

The platelet production method according to the present invention is characterized in that it uses a culture produced by the production method described above. In a more specific embodiment, the platelet production method according to the present invention contains a step of culturing the megakaryocytes, megakaryocyte progenitor cells, and/or megakaryocyte cell line obtained by the method described above and recovering platelets from the culture.

The culture conditions are not limited, but, for example, cultivation may be carried out in the presence of TPO (10 to 200 ng/mL and preferably about 50 to 100 ng/mL) or in the presence of TPO (10 to 200 ng/mL and preferably about 50 to 100 ng/mL), SCF (10 to 200 ng/mL and preferably about 50 ng/mL), and heparin (10 to 100 U/mL and preferably about 25 U/mL).

The culture time is desirably at least 3 days, but is not particularly limited as long as the functionality of the produced platelets is maintained. The culture time is, for example, 3 to 14 days. The culture time is preferably 4 to 12 days and is more preferably 5 to 10 days.

The culture temperature is not particularly limited and, for example, is 35.0° C. to 42.0° C. A culture temperature of 36.0° C. to 40° C. is preferred while 37.0° C. to 39.0° C. is more preferred.

The megakaryocyte culture step may be carried out in the production method according to the present invention under serum-free and/or feeder cell-free conditions. This is preferably a method in which megakaryocytes produced according to the method of the present invention are cultured on a TPO-containing culture medium. When feeder cells are not used, a conditioned medium may be used in an embodiment. The conditioned medium, although not particularly limited, can be prepared by a person skilled in the art using known methods, and so forth; for example, feeder cells can be cultured as appropriate and the conditioned medium can be obtained by removing the feeder cells from the culture using a filter.

A ROCK inhibitor and/or an inhibitor of actomyosin complex functionality is added to the culture medium in an embodiment of the platelet production method according to the present invention. The ROCK inhibitor and inhibitor of actomyosin complex functionality can be the same as those used in the multinucleated megakaryocyte production method described above. The ROCK inhibitor can be exemplified by Y27632, fasudil hydrochloride, and H1152 dihydrochloride. The inhibitor of actomyosin complex functionality can be exemplified by myosin ATPase activity inhibitors and myosin light-chain kinase inhibitors. Examples are blebbistatin, ML-7, and ML-9. A ROCK inhibitor or inhibitor of actomyosin complex functionality may be added by itself or the combination of a ROCK inhibitor and an inhibitor of actomyosin complex functionality may be added.

The ROCK inhibitor and/or inhibitor of actomyosin complex functionality may be added at, for example, 0.1 to 30.0 µM. The inhibitor concentration is preferably 0.5 to 25.0 µM, more preferably 1.0 to 20.0 µM, and still more preferably 5.0 to 15.0 µM.

The culture time with the addition of a ROCK inhibitor and/or inhibitor of actomyosin complex functionality can be, for example, 1 to 15 days. The culture time is preferably 3 to 13 days, more preferably 5 to 11 days, and still more preferably 6 days, 7 days, 8 days, 9 days, or 10 days. Additional increases in the proportion of CD42b-positive platelets can be brought about by the addition of a ROCK inhibitor and/or inhibitor of actomyosin complex functionality.

The platelets can be separated from the culture medium by methods known to a person skilled in the art. The platelets obtained in accordance with the present invention are very safe platelets that do not express exogenous genes. The megakaryocytes provided by the present invention, while not particularly limited, may express, for example, an exogenous apoptosis suppressor gene and cancer gene. In such a case, a condition is set up in the platelet production step whereby the expression of the exogenous genes is inhibited.

The platelets provided by the present invention may be administered to a patient as a formulation. Depending on the administration, platelets obtained using the method of the present invention may be stored and formulated using, for example, human plasma, an infusion solution, citrated physiological saline, a solution based on glucose-supplemented Ringer's acetate solution, PAS (platelet additive solution) (Gulliksson, H. et al., Transfusion, 32:435-440 (1992)), and so forth. The storage period is about 14 days from immediately after formulation. Ten days is preferred. Eight days is more preferred. With regard to the storage conditions, storage is desirably carried out with shake agitation at room temperature (20° C. to 24° C.).

A more detailed description follows using examples, but the present invention is in no way limited by the examples.

EXAMPLES

1. Preparation of Hematopoietic Progenitor Cells from iPS Cells

Differentiation culture to blood cells was carried out from human iPS cells (692D2, 1108A2: iPS cells derived from peripheral blood mononuclear cells and established using the episomal vector described in Okita K., et al., Stem Cells 31, 458-66, 2012; TKDN SeV2: iPS cells derived from human fetal skin fibroblasts and established using Sendai virus) using the method described in Takayama N., et al., J. Exp. Med. 2817-2830 (2010). Thus, human ES/iPS cell colonies were cocultured for 14 days with C3H10T1/2 feeder cells in the presence of 20 ng/mL VEGF (R&D Systems, Inc.) to produce hematopoietic progenitor cells (HPC). The culture conditions were 20% $O_2$ and 5% $CO_2$ (these same conditions apply in the following unless specifically indicated otherwise).

2. Viral Infection of c-MYC and BMI1 into the Hematopoietic Progenitor Cells $5 \times 10^4$ cells/well of the HPC cells obtained by the above-described method were seeded into 6-well plates that had been seeded in advance with C3H10T1/2 feeder cells, and the overexpression of c-MYC and BMI1 was carried out using the lentivirus method. In this case, 6 wells were used per cell line. Thus, the virus particles were added to the culture medium to provide an MOI of 20 for each, and infection was carried out by spin infection (32° C., 900 rpm, centrifugation for 60 minutes). This operation was carried out twice with a 12 hour interval. The medium used here was obtained by the addition of protamine at a final concentration of 10 µg/mL to a medium (referred to below as the differentiation medium) prepared by the incorporation of 50 ng/mL human thrombopoietin (TPO) (R&D Systems, Inc.), 50 ng/mL human stem cell factor (SCF) (R&D Systems, Inc.), and 2 µg/mL doxycycline (Dox) into a base medium (IMDM (Iscove's Modified Dulbecco's Medium) (Sigma-Aldrich Corporation) containing 15% fetal bovine serum (GIBCO), 1% penicillin-streptomycin-glutamine (GIBCO), 1% insulin, transferrin, selenium solution (ITS-G) (GIBCO), 0.45 mM 1-thioglycerol (Sigma-Aldrich Corporation), and 50 µg/mL L-ascorbic acid (Sigma-Aldrich Corporation)). The lentivirus vectors (respectively, LV-TRE-c-MYc-Ubc-tTA-I2G, LV-TRE-BMI1-Ubc-tTA-I2G, and LV-TRE-BCL-xL-Ubc-tTA-I2G) were tetracycline-controlled inducible vectors and were constructed by the recombination of c-MYC, BMI1, and BCL-xL with the mOKS cassette of LV-TRE-mOKS-Ubc-tTA-I2G (Kobayashi, T., et al., Cell 142, 787-799 (2010)). The virus particles used for infection were produced by expressing the lentivirus vectors in 293T cells.

3. Production of Megakaryocyte Self-Replicating Lines and Maintenance Culture

Megakaryocyte self-replicating lines derived from 692D2 and 1108A2 were respectively produced by culturing, as described below, the cMYC and BMI1 gene-transduced megakaryocyte cells, using the day on which the cMYC and BMI1 viral infection was performed by the aforementioned method as infection day 0.

Infection Day 2 to Infection Day 11

The post-viral-infection blood cells obtained by the method described above were recovered by pipetting; centrifugation was carried out for 5 minutes at 1200 rpm; the supernatant was removed; suspension was then performed in fresh differentiation medium; and seeding (6-well plate) was carried out on fresh C3H10T1/2 feeder cells. Subculturing was performed by carrying out the same procedure on infection day 9. After measuring the cell count, seeding (6-well plate) was performed onto C3H10T1/2 feeder cells at $1 \times 10^5$ cells/2 mL/well.

Infection Day 12 to Infection Day 13

The same procedure as on infection day 2 was performed. After measuring the cell count, seeding (100-mm dish) onto C3H10T1/2 feeder cells was performed at $3 \times 10^5$ cells/10 mL/100-mm dish.

Infection Day 14

The post-viral-infection blood cells were recovered and were subjected to an antibody reaction with, per $1.0 \times 10^5$ cells, 2 µL, 1 µL, and 1 µL, respectively, of anti-human CD41a-APC antibody (BioLegend, Inc.), anti-human CD42b-PE antibody (eBioscience), and anti-human CD235ab-Pacific Blue (BioLegend, Inc.) antibody. After the reaction, analysis was carried out using a FACSVerse™ (BD). A megakaryocyte self-replicating line was produced when the CD41a-positive ratio at infection day 14 was at least 50%.

4. BCL-xL Viral Infection of Megakaryocyte Self-Replicating Lines

BCL-xL gene transduction was performed by the lentivirus method on the culture day 14 post-virus-infection blood cells. The virus particles were added to the culture medium to provide an MOI of 10, and infection was achieved by spin infection (32° C., 900 rpm, centrifugation for 60 minutes).

5. Preparation of Immortalized Megakaryocyte Lines and Maintenance Culture

Infection Day 14 to Infection Day 18

The post-viral-infection blood cells yielded by the above-described method were recovered and were subjected to a centrifugation procedure for 5 minutes at 1200 rpm. After centrifugation, the sedimented cells were suspended in fresh differentiation medium and were subsequently seeded (6-well plate) at $2 \times 10^5$ cells/2 mL/well onto fresh C3H10T1/2 feeder cells.

Infection Day 18: Subculture

After measuring the cell count, seeding was carried out at $3 \times 10^5$ cells/10 mL/100-mm dish.

Infection Day 24: Subculture

After measuring the cell count, seeding was carried out at $1 \times 10^5$ cells/10 mL/100-mm dish. Subsequent to this, maintenance culture was carried out by subculturing every 4 to 7 days.

The blood cells were recovered on infection day 24 and were subjected to immunostaining using, per $1.0 \times 10^5$ cells, 2 μL, 1 μL, and 1 μL, respectively, of anti-human CD41a-APC antibody (BioLegend, Inc.), anti-human CD42b-PE antibody (eBioscience), and anti-human CD235ab-Pacific Blue (Anti-CD235ab-PB; BioLegend, Inc.) antibody. This was followed by analysis using a FACSVerse™ (BD). Lines that had a CD41a-positive ratio of at least 50% even on infection day 24 were considered to be immortalized megakaryocyte cell lines.

Cells derived from iPS cells (692D2, 1108A2) could be propagated for at least 24 days post-infection as a result of the maintenance culture of the cells that had undergone BCL-xL lentivirus infection. These cells were regarded as immortalized megakaryocyte lines (Comparative Examples 1 and 2). An immortalized megakaryocyte line was also produced with TKDN SeV2 using the same procedure (Comparative Example 3).

It was confirmed that all of the immortalized megakaryocyte lines of Comparative Examples 1 to 3 could be subcultured for at least 40 days. It was also confirmed, on the other hand, that the culture process was accompanied by an increase in cells transformed to adherent cells.

6. Construction of a Drug Resistance Gene Expression Vector Using a Megakaryocyte-Specific Gene Expression Promoter The LV-TetON vector (Clontech Laboratories, Inc.), a CD41a promoter sequence (SEQ ID NO: 1) cloned from KhES3 cells (established at Kyoto University), and a puromycin resistance gene sequence subcloned from pENTR-DMD-Donor04_EF1a-Puro were then recombined into CS-CDF-UG-PRE that had been digested with the restriction enzymes EcoRI and XhoI. This recombination was carried out using an In-Fusion Advance PCR cloning kit (Clontech Laboratories, Inc.). A lentivirus vector containing the CD41a promoter-puromycin resistance gene (FIG. 1) could be constructed as a result.

7. Gene Transduction Using the Lentivirus Vector Containing the CD41a Promoter-Puromycin Resistance Gene HEK293T cells were transfected with the lentivirus vector containing the CD41a promoter-puromycin lentivirus resistance gene. Lentivirus containing the CD41a promoter-puromycin resistance gene was then concentrated and produced from the culture supernatant of the transfected HEK293T cells. The immortalized megakaryocyte cell line, seeded at $2 \times 10^6$ cells/10 mL/dish onto C3H10T1/2 cells (feeder cells) in a 10-cm dish, were infected at an MOI of 10 with the lentivirus containing the CD41a promoter-puromycin resistance gene. After infection, the immortalized megakaryocyte cell line was static cultured under conditions of 37° C. and 5% $CO_2$ using a culture medium (puromycin-containing differentiation medium) provided by the incorporation of 2 μg/mL puromycin into a medium (differentiation medium) that contained 50 ng/mL human thrombopoietin (TPO) (R&D Systems, Inc.), 50 ng/mL human stem cell factor (SCF) (R&D Systems, Inc.), and 2 μg/mL doxycycline (Dox) in a base medium (IMDM (Iscove's Modified Dulbecco's Medium) (Sigma-Aldrich Corporation) containing 15% fetal bovine serum (GIBCO), 1% penicillin-streptomycin-glutamine (GIBCO), 1% insulin, transferrin, selenium solution (ITS-G) (GIBCO), 0.45 mM 1-thioglycerol (Sigma-Aldrich Corporation), and 50 μg/mL L-ascorbic acid (Sigma-Aldrich Corporation)).

The cell lines transduced by the lentivirus containing the CD41a promoter-puromycin resistance gene were designated Example 1 (692D2 origin), Example 2 (1108A2 origin), and Example 3 (TKDN SeV2 origin).

8. Analysis of Megakaryocyte Markers (in the Presence of Feeder Cells)

Figure 2:
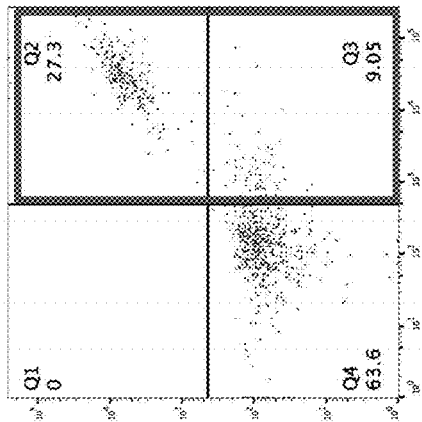
FIG. 2 illustrates confirmation by flow cytometry of the differentiation phenotype of megakaryocyte cells after the introduction of a CD41a promoter-puromycin resistance gene.
Figure 2:
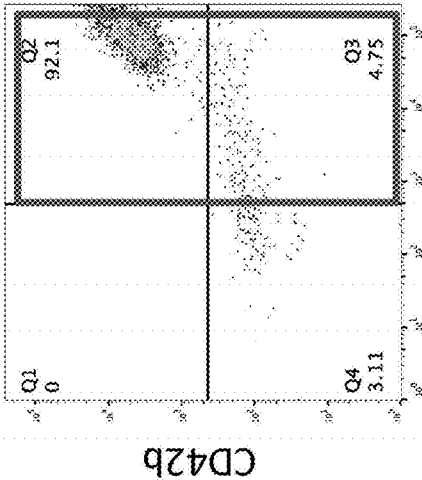
Figure 3:
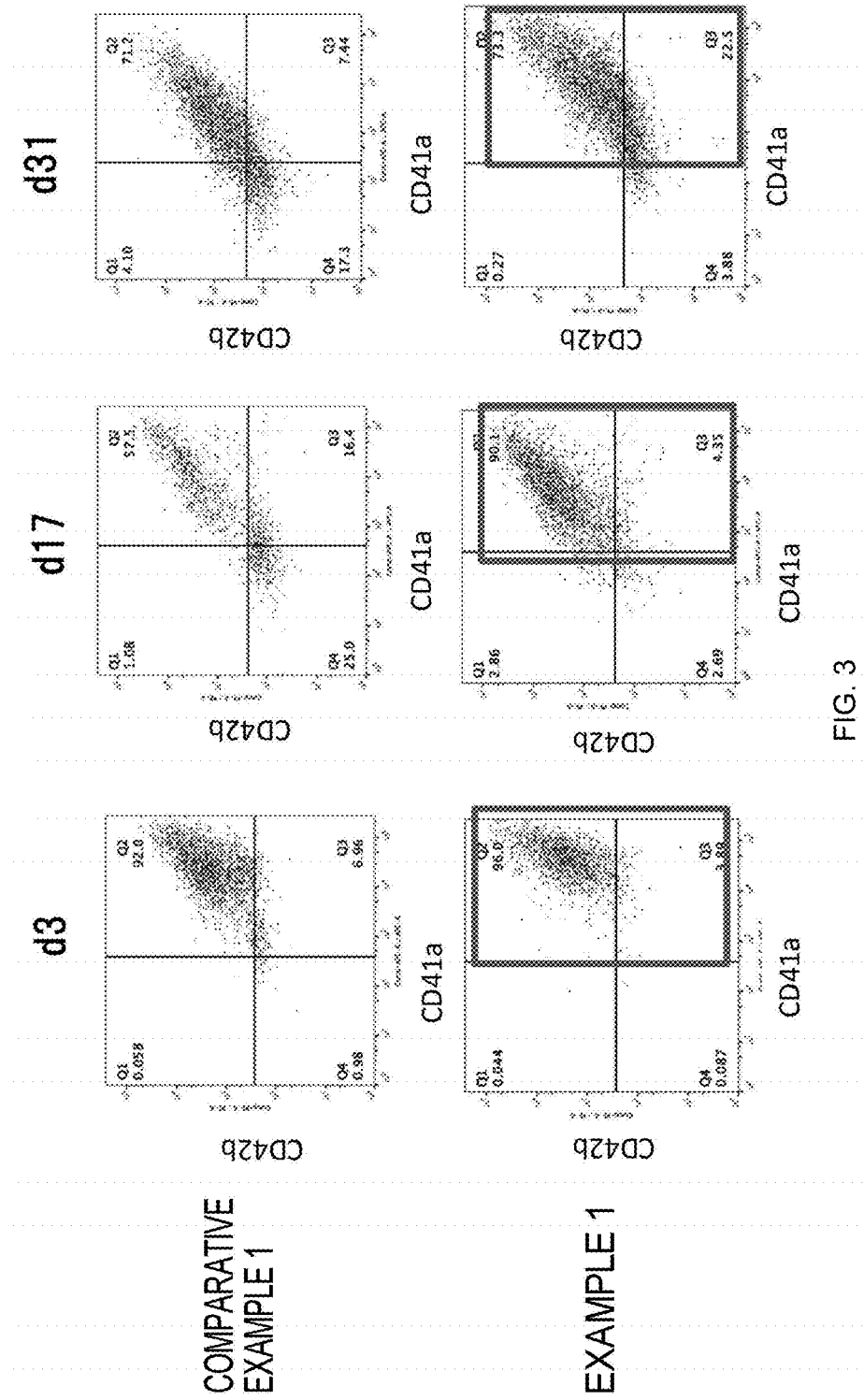
FIG. 3 illustrates confirmation by flow cytometry of a CD41a-positive phenotype for megakaryocyte cells obtained in the presence of feeder cells.
Figure 4:
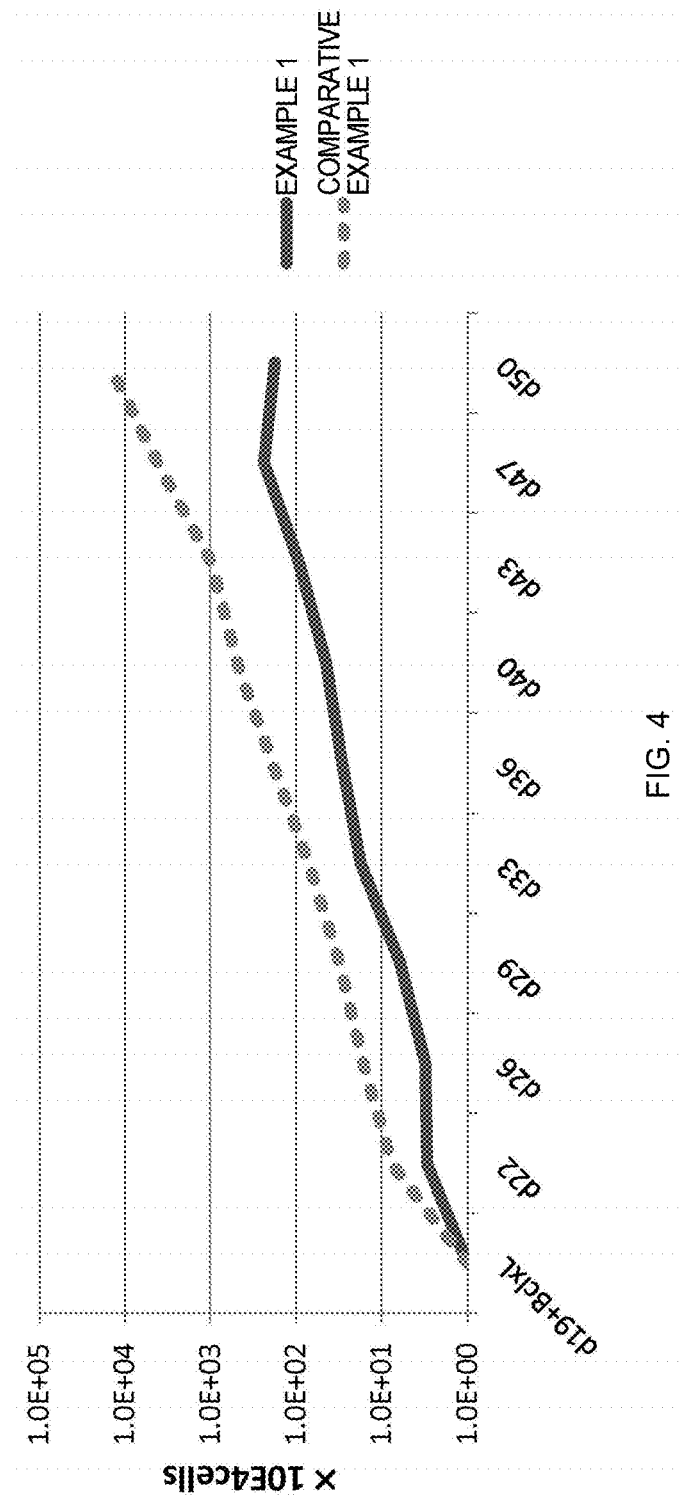
FIG. 4 illustrates a change in cell count with elapsed culture time after the introduction of a CD41a promoter-puromycin resistance gene.

The cells were stained using CD41a antibody (anti-CD41-APC, BioLegend, Inc.), CD42b antibody (anti-CD42b, eBioscience), and CD235ab antibody (anti-CD235ab-PB, BioLegend, Inc.) and were analyzed using a BD FACSVerse™ flow cytometer. According to the results, the cell group transduced with the lentivirus containing the CD41a promoter-puromycin resistance gene (Example 1) had a higher CD41a-positive ratio than the nontransduced cell group (Comparative Example 1) (FIG. 2). Even during the continuation of culture after this, the culture obtained by the cultivation of the cell group of Example 1 exhibited a higher CD41a-positive ratio than in Comparative Example 1 (FIG. 3). The CD41a-positive cell count in Example 1 continued to increase (FIG. 4).

9. Analysis of Megakaryocyte Markers (in the Absence of Feeder Cells)

Figure 5:
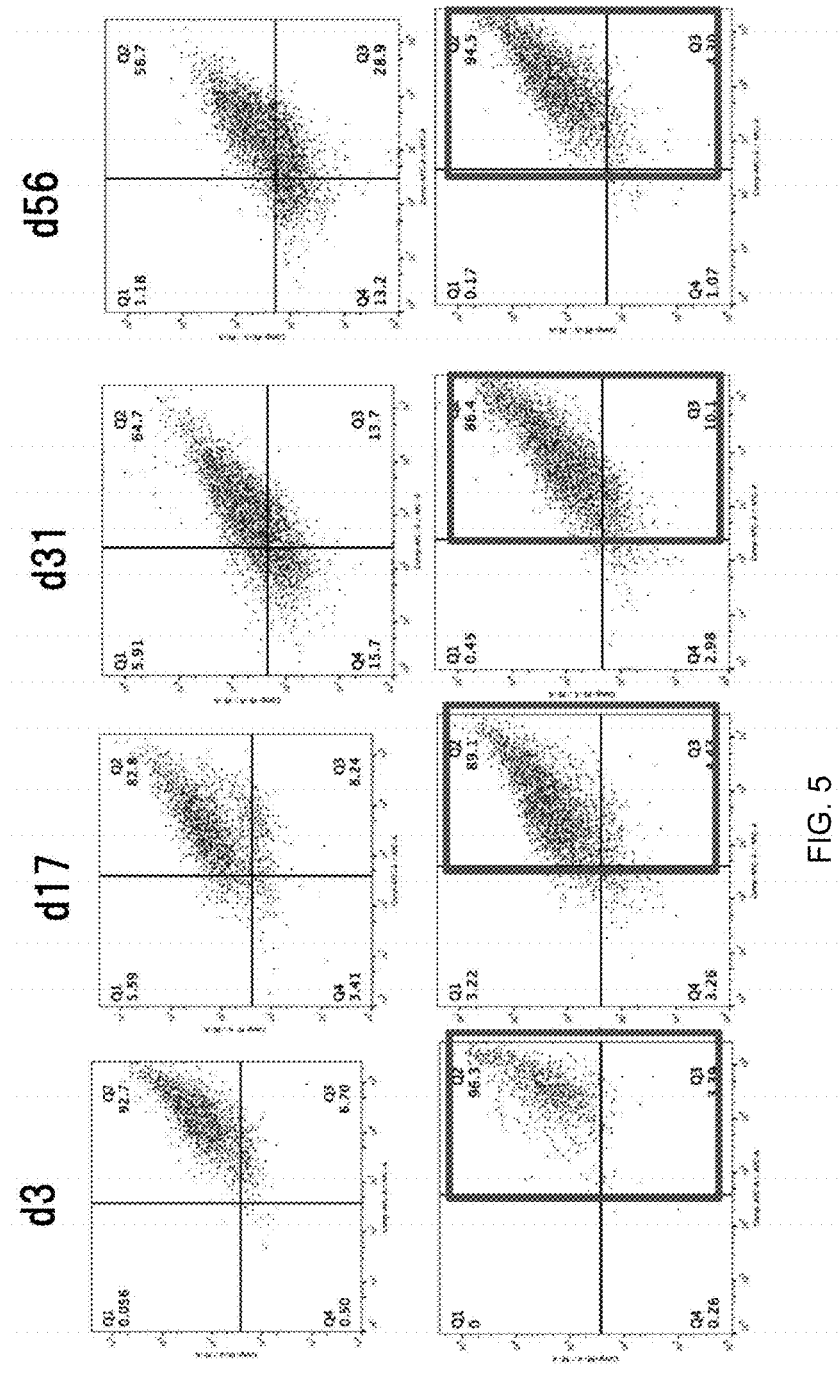
FIG. 5 illustrates confirmation by flow cytometry of the CD41a-positive phenotype of megakaryocyte cells obtained in the absence of feeder cells.

The 1108A2-derived cell line transduced by the lentivirus having the CD41a promoter-puromycin resistance gene was prepared under the same conditions as in Example 1, but without using feeder cells during culture (Example 2). Comparative Example 2 was the nontransduced cell line derived from 1108A2. Even in the case of culture without using feeder cells, the culture obtained by cultivation of the cell group of Example 2 was able to exhibit a higher CD41a-positive ratio than in Comparative Example 2 (FIG. 5).

10. Comparison of the Presence of Feeder Cells with the Absence of Feeder Cells

Figure 6A:
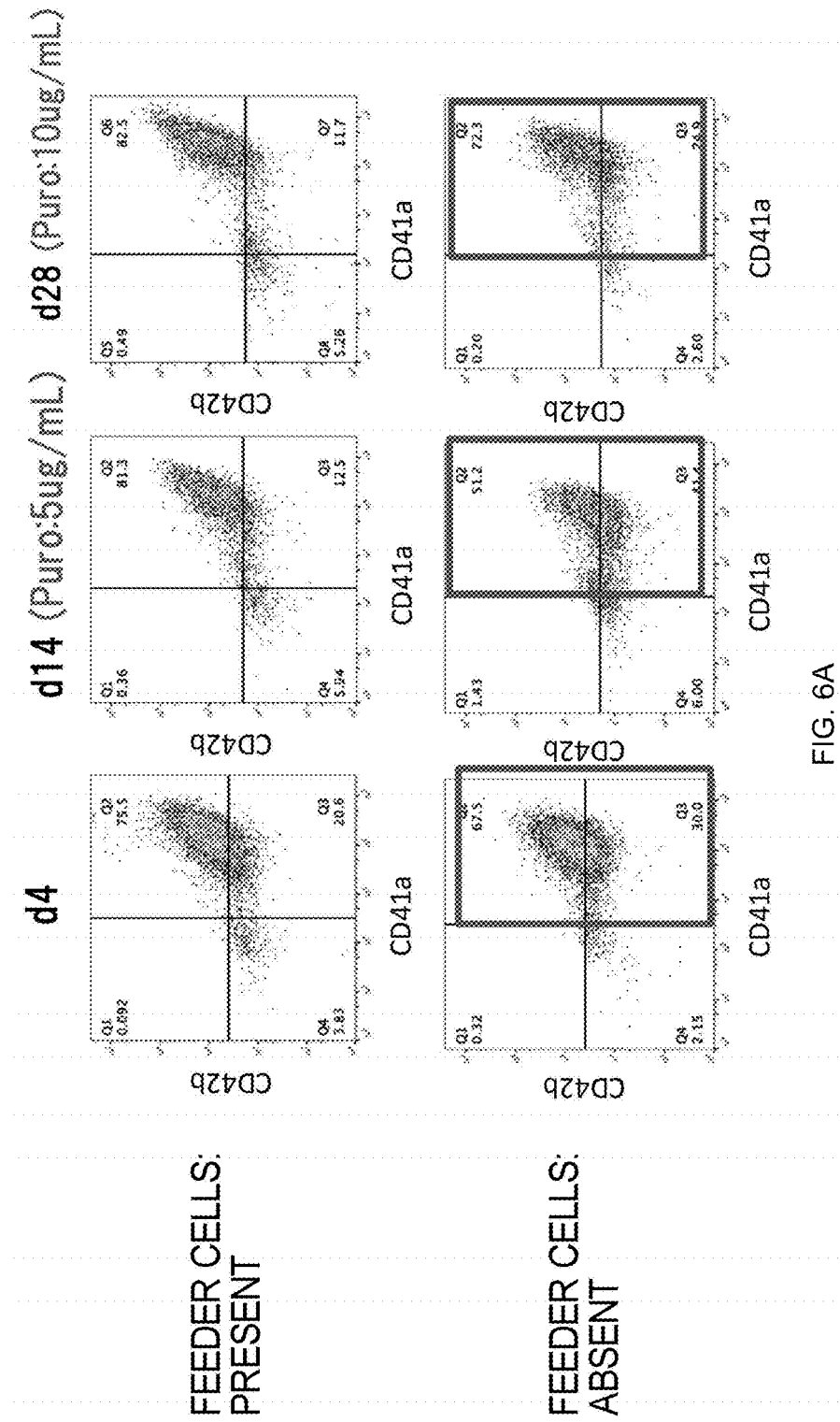
FIG. 6A illustrates a comparison, by flow cytometry, of the CD41a-positive phenotype of megakaryocyte cells obtained in the presence and in the absence of feeder cells.
Figure 6B:
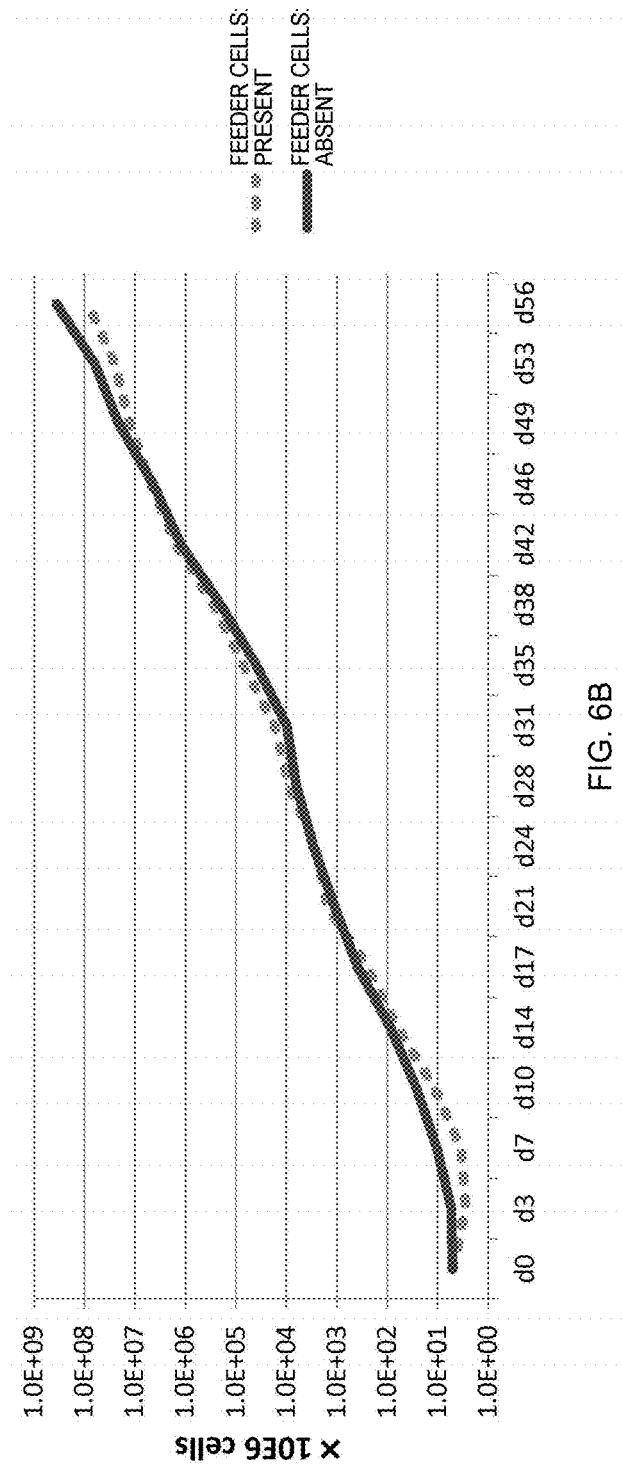
FIG. 6B illustrates a comparison of the change in cell count with elapsed culture time after the introduction of a CD41a promoter-puromycin resistance gene, in the presence of feeder cells versus in the absence of feeder cells.

For the 692D2-derived Example 1, a high CD41a-positive ratio was observed (FIG. 6A) for both conditions, i.e., in the presence of feeder cells and in the absence of feeder cells, even when the concentration of puromycin present in the culture medium for the cell line was increased to, respectively, 5 μg/m L at culture day 14 and 10 μg/mL at culture day 28. In addition, the change in cell count was measured with elapsed time in each case. The cell count was measured using a hemocytometer (Waken BTech Co., Ltd.) with the cultured cells diluted with a 0.1% (v/v) Trypan Blue solution. The results demonstrated that the cells propagated with elapsed time at about the same rate regardless of the presence/absence of feeder cells (FIG. 6B).

11. Measurement of Cell Propagation (Shake Culture)

Figure 7:
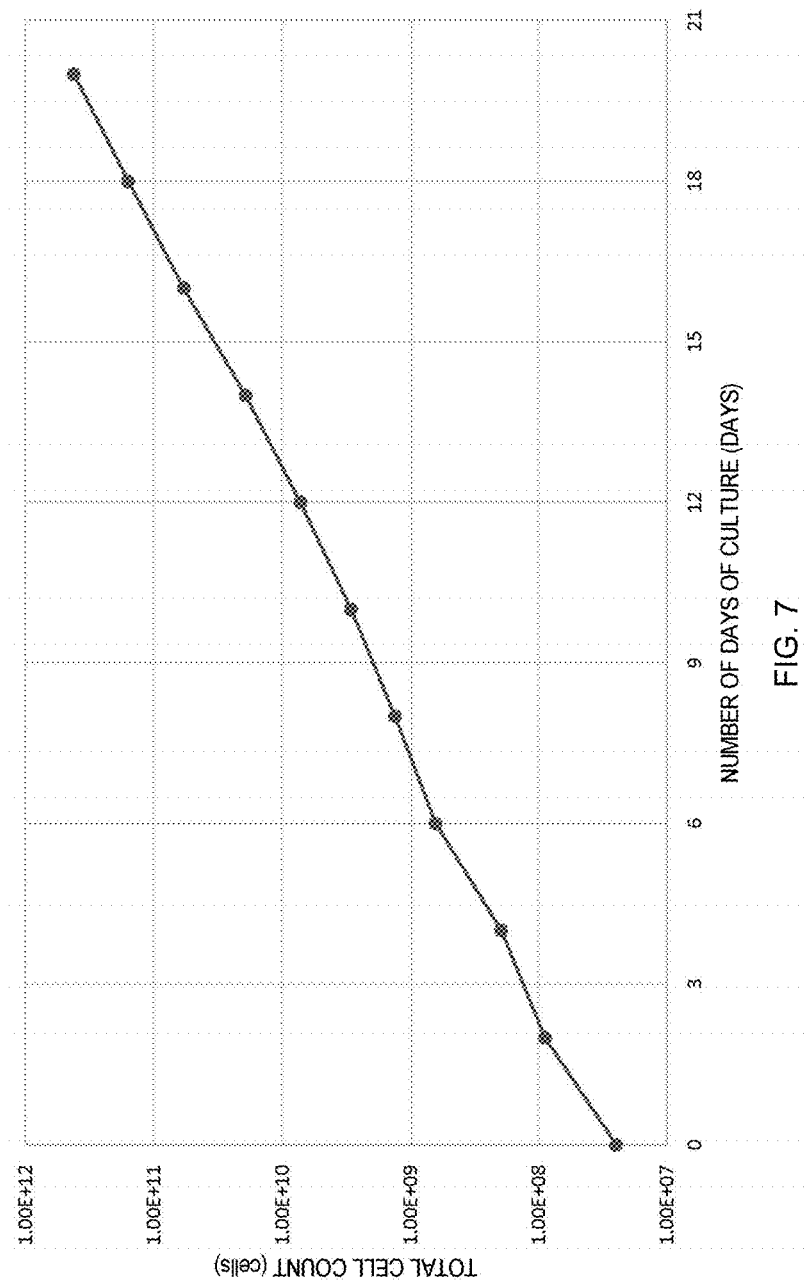
FIG. 7 illustrates a change in cell count with elapsed culture time in shake culture (flask).
Figure 8:
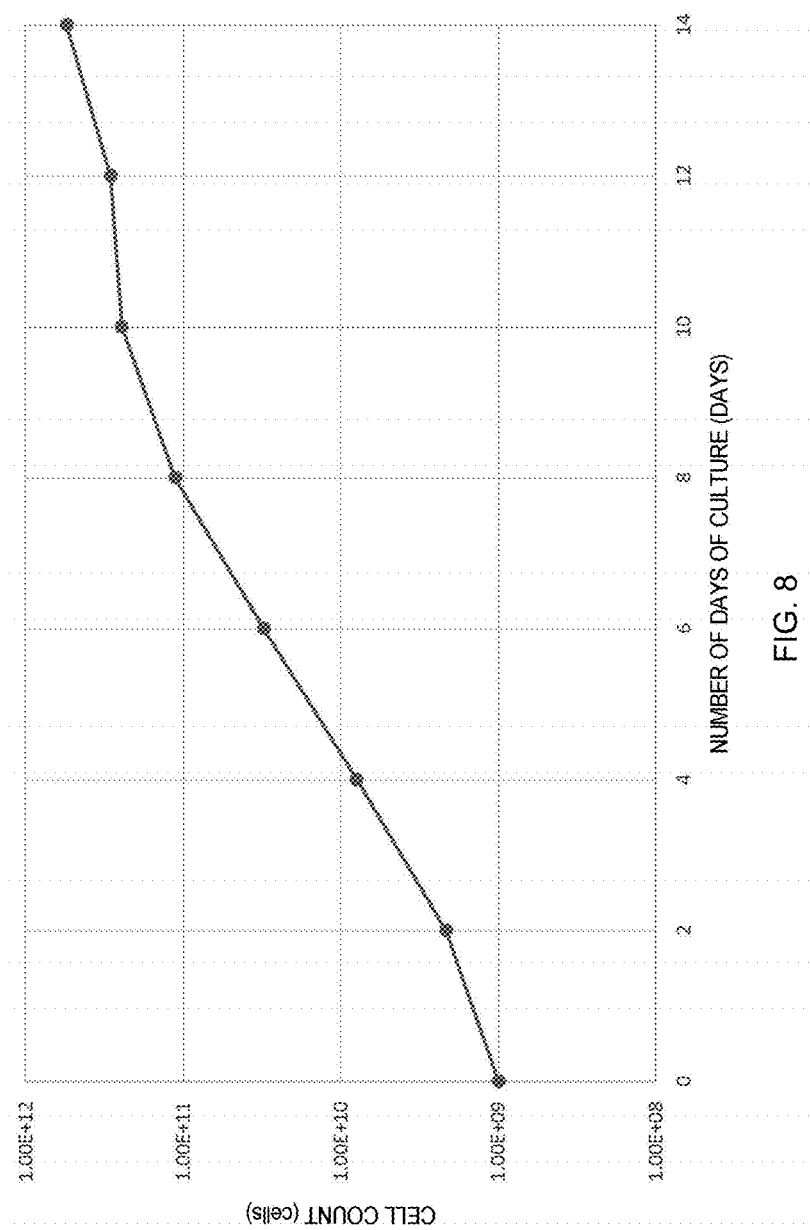
FIG. 8 illustrates a change in cell count with elapsed culture time in shake culture (bag).

The 692D2-derived cell line transduced by the lentivirus having the CD41a promoter-puromycin resistance gene was prepared under the same conditions as in Example 1, but using flask culture and bag culture for the culture method (flask culture: Example 4; bag culture: Example 5). According to the results, the CD41a-positive cell ratio underwent a significant increase in the cultures obtained by culturing the cell groups in Example 4 and Example 5 (FIG. 7 (Example 4), FIG. 8 (Example 5)).

12. Measurement of the Platelet Count (Static Culture, in the Presence of Feeder Cells)

Figure 9:
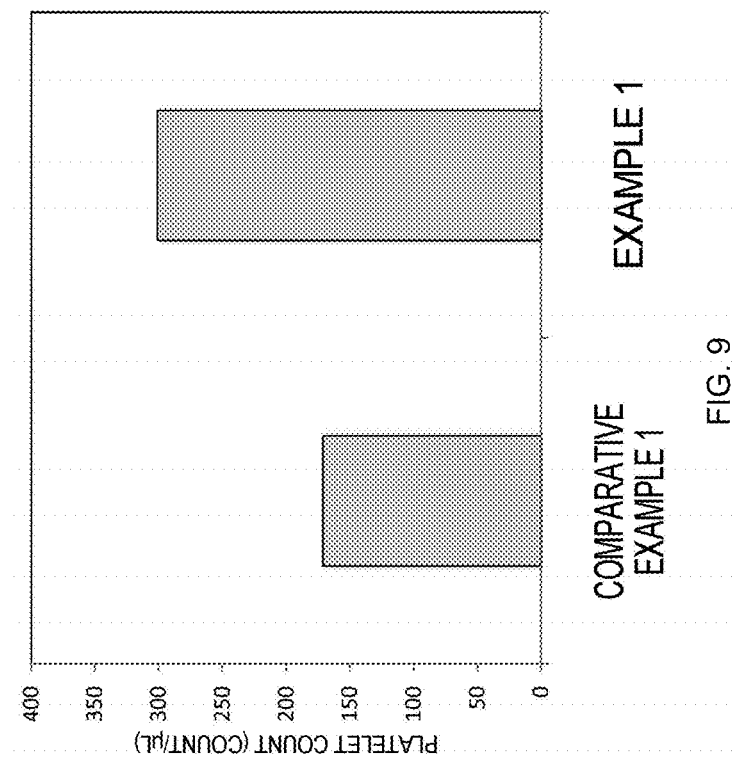
FIG. 9 illustrates the number of platelets produced for megakaryocyte cells obtained in the presence of feeder cells.

The platelets present in the culture supernatant were stained with CD41a antibody (anti-CD41-APC, BioLegend, Inc.), CD42a antibody (anti-CD42a, eBioscience), and CD42b antibody (anti-CD42b, eBioscience) and analysis was performed using a BD FACSVerse™ flow cytometer. According to the results, the cell group transduced with the CD41a promoter-puromycin resistance gene (Example 1) had a CD41a-positive, CD42b-positive platelet productivity (number of platelets produced per seeded cell) that was at least twice as high as that for the nontransduced cell group (Comparative Example 1) (Table 1, FIG. 9).

TABLE 1

| | feeder cells | platelet count | | | |
|---|---|---|---|---|---|
| | | count | AV | /μL | /seeded cell count |
| Comparative Example 1 | + | 866 | 866 | 144 | 1.4 |
| Example 1 | + | 1977 | 1977 | 330 | 3.3 |

13. Measurement of the Platelet Count (Static Culture, in the Absence of Feeder Cells)

Figure 10:
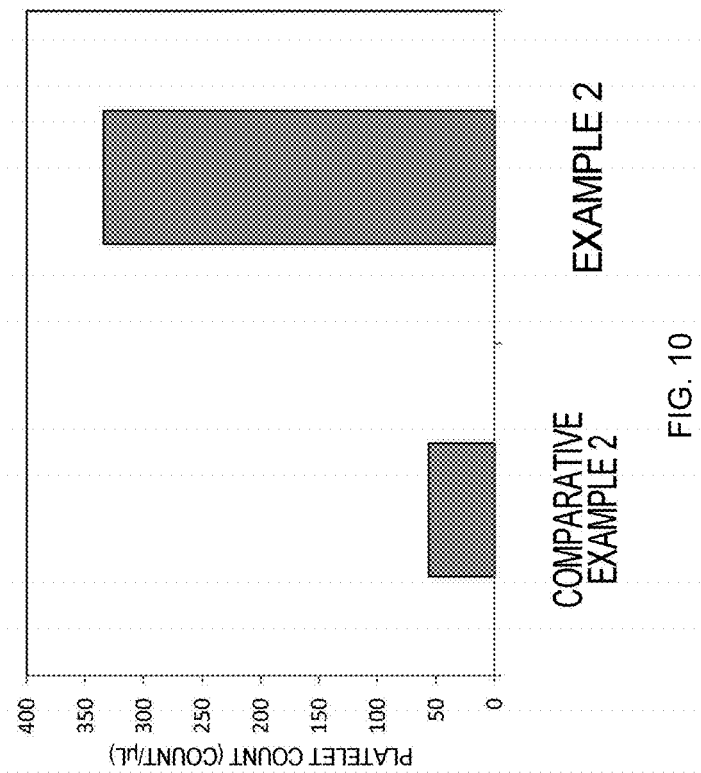
FIG. 10 illustrates the number of platelets produced for megakaryocyte cells obtained in the absence of feeder cells.

The enhancement in the CD41a-positive, CD42b-positive platelet productivity (number of platelets produced per seeded cell) was also confirmed for the case of platelet production without any use of feeder cells. The cell group transduced with the CD41a promoter-puromycin resistance gene (Example 2) had a platelet productivity that was about five-times higher than the nontransduced cell group (Comparative Example 2) (Table 2, FIG. 10).

TABLE 2

| | feeder cells | platelet count | | | |
|---|---|---|---|---|---|
| | | count | AV | /μL | /seeded cell count |
| Comparative Example 2 | − | 340 | 340 | 57 | 0.6 |
| Example 2 | − | 2007 | 2007 | 335 | 3.3 |

What is claimed is:

1. A method for obtaining megakaryocyte progenitor cells that differentiate into megakaryocytes having increased platelet productivity, the method comprising:
   a) providing megakaryocyte progenitor cells that have been differentiated from induced pluripotent stem cells, said progenitor cells have a lethal gene positioned under the control of a promoter of a gene that encodes a CD235 protein; and
   b) culturing the progenitor cells for at least 18 days and until at least 50% of the progenitor cells are CD41a-positive, wherein the culturing conditions cause the death of cells in which said promoter functions, thereby obtaining megakaryocyte progenitor cells that differentiate into megakaryocytes having increased platelet productivity.

2. The method according to claim 1, wherein the lethal gene is an HSV-TK gene.

3. The method according to claim 1, wherein the culturing is carried out in the absence of serum and/or feeder cells.

4. The method according to claim 1, which further comprises differentiating the obtained megakaryocyte progenitor cells into megakaryocytes.

5. The method according to claim 4, wherein the progenitor cells are hematopoietic stem cells, hematopoietic progenitor cells, CD34-positive cells, or megakaryocyte progenitor cells.

6. The method according to claim 4, which further comprises transforming the progenitor cells with the lethal gene.

7. The method according to claim 4, wherein the progenitor cells are transformed with a vector in which the promoter and lethal gene are operably linked.

* * * * *

SEQUENCE LISTING

```
<160> NUMBER OF SEQ ID NOS: 1

<210> SEQ ID NO 1
<211> LENGTH: 948
<212> TYPE: DNA
<213> ORGANISM: Homo sapiens

<400> SEQUENCE: 1
tgtgaacgga ccaagagtaa acagtgtgct caatgctgtg cctacgtgtg ttagcccacg      60
cggccagcct gaggagtcag ggaaggctcc cctaggcaaa gcccccaacc agaatcaagt     120
cttaatggtt aaagagctcc atcacccaaa aaggattgag ggcctacctt caactgaaca     180
gctaatgcat aatctcagaa actgtgagtc aaaattccct ggaataactc cactttatcc     240
ccaatctcct tgccacctag accaaggtcc attcaccacc ctgtccccag cactgactgc     300
actgctgtgg ccacactaaa gcttggctca agacggagga ggagtgagga agctgctgca     360
ccaatatggc tggttgaggc cgcccaaggt cctagaagga ggaagtgggt aaatgccata     420
tccaaaaaga tacagaagcc tcaggtttta tcgggggcag cagcttcctt ctccttcccc     480
gacctgtggc caagtcacaa agcaccacag ctgtacagcc agatggggga agggaggaga     540
ttagaactgt aggctagagt agacaagtat ggaccagttc acaatcacgc tatcccaagc     600
agaaagtgat ggtggcttgg actagcacgg tggtagtaga gatggggtaa agattcaaga     660
gacatcattg ataggcagaa ccaataggac atggtaataa actattctca ggaaaggggga    720 ggagtcatgg ctttcagcca tgagcatcca ccctctgggt ggcctcaccc acttcctggc     780
aattctagcc accatgagtc cagggctat agcccttttgc tctgcccgtt gctcagcaag     840
ttacttgggg ttccagtttg ataagaaaag acttcctgtg gaggaatctg aagggaagga     900
ggaggagctg gcccattcct gcctgggagg ttgtggaaga aggaagat                  948
```